(12) United States Patent
Kaneko et al.

(10) Patent No.: US 8,048,928 B2
(45) Date of Patent: Nov. 1, 2011

(54) THERAPEUTIC AGENT FOR TREATING LIVER DISEASE CONTAINING 2-AMINO-1,3-PROPANEDIOL DERIVATIVE AS ACTIVE INGREDIENT, AND METHOD FOR TREATING LIVER DISEASE

(75) Inventors: Takashi Kaneko, Tokyo (JP); Eiji Kobayashi, Tochigi (JP); Tokutarou Yasue, Ibaraki (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 173 days.

(21) Appl. No.: 12/083,224

(22) PCT Filed: Oct. 5, 2006

(86) PCT No.: PCT/JP2006/319961
§ 371 (c)(1),
(2), (4) Date: Apr. 7, 2008

(87) PCT Pub. No.: WO2007/043433
PCT Pub. Date: Apr. 19, 2007

(65) Prior Publication Data
US 2009/0253802 A1    Oct. 8, 2009

(30) Foreign Application Priority Data
Oct. 7, 2005    (JP) .................................. 2005-295478

(51) Int. Cl.
*A61K 31/137*    (2006.01)
(52) U.S. Cl. ....................................................... 514/653
(58) Field of Classification Search ......................... None
See application file for complete search history.

(56) References Cited

U.S. PATENT DOCUMENTS

| | | | |
|---|---|---|---|
| 5,447,922 A | 9/1995 | Lawrence et al. | |
| 5,604,229 A | 2/1997 | Fujita et al. | |
| 5,948,820 A | 9/1999 | Fujita et al. | |
| 6,004,565 A | 12/1999 | Chiba et al. | |
| 6,214,873 B1 | 4/2001 | Adachi et al. | |
| 6,489,331 B1 | 12/2002 | Shimada et al. | |
| 6,531,505 B2 | 3/2003 | Xu et al. | |
| 6,667,025 B2 * | 12/2003 | Chiba et al. | 424/9.1 |
| 6,960,692 B2 | 11/2005 | Kohno et al. | |
| 6,963,012 B2 | 11/2005 | Kohno et al. | |
| 7,456,157 B2 | 11/2008 | Kohno et al. | |
| 7,482,491 B2 | 1/2009 | Kohno et al. | |
| 7,781,617 B2 * | 8/2010 | Kudou et al. | 564/336 |
| 7,807,854 B2 * | 10/2010 | Kudou et al. | 564/336 |
| 2002/0040050 A1 | 4/2002 | Xu et al. | |
| 2002/0091105 A1 | 7/2002 | Mandala et al. | |
| 2002/0143034 A1 | 10/2002 | Taniguchi et al. | |
| 2003/0069168 A1 | 4/2003 | Xu et al. | |
| 2003/0236297 A1 | 12/2003 | Nishi et al. | |
| 2004/0058894 A1 | 3/2004 | Doherty et al. | |
| 2004/0067908 A1 | 4/2004 | Nakade et al. | |
| 2004/0087662 A1 | 5/2004 | Bigaud et al. | |
| 2004/0110728 A1 | 6/2004 | Macdonald et al. | |
| 2004/0138462 A1 | 7/2004 | Sakurai et al. | |
| 2004/0147305 A1 | 7/2004 | Albert et al. | |
| 2004/0224941 A1 | 11/2004 | Seko et al. | |
| 2004/0235794 A1 | 11/2004 | Nakade et al. | |
| 2004/0242654 A1 | 12/2004 | Kohno et al. | |
| 2004/0248952 A1 | 12/2004 | Pan et al. | |
| 2004/0254222 A1 | 12/2004 | Kohno et al. | |
| 2005/0009786 A1 | 1/2005 | Pan et al. | |
| 2005/0020837 A1 | 1/2005 | Doherty et al. | |
| 2005/0033055 A1 | 2/2005 | Bugianesi et al. | |
| 2005/0043386 A1 | 2/2005 | Nishi et al. | |
| 2005/0107345 A1 | 5/2005 | Doherty et al. | |
| 2005/0222422 A1 | 10/2005 | Lynch et al. | |
| 2005/0245575 A1 | 11/2005 | Chen et al. | |
| 2006/0046979 A1 | 3/2006 | Foster et al. | |
| 2006/0089334 A1 | 4/2006 | Budhu et al. | |
| 2006/0135622 A1 | 6/2006 | Kohno et al. | |
| 2006/0135786 A1 | 6/2006 | Saha et al. | |
| 2006/0148830 A1 | 7/2006 | Terakado et al. | |
| 2006/0148844 A1 | 7/2006 | Nakade et al. | |
| 2006/0160771 A1 | 7/2006 | Kohno et al. | |

(Continued)

FOREIGN PATENT DOCUMENTS

JP    2000-154151    6/2000

(Continued)

OTHER PUBLICATIONS

Vippagunta (Adv. Drug Del. Rev., 2001, vol. 48, 2001, pp. 3-26.*
Rakela, BJ, Rev. Med. Chil., (Apr. 2010); 138(4):504-10 (abstract).*
Tovoli et al., Case Rep. Gastroenterology, (Oct. 2010); 4(3):469-475 (Abstract).*
The Merck Manual, 17th edition, (1999), pp. 343-344.*
International Search Report issued Nov. 28, 2006 in the International (PCT) Application PCT/JP2006/319961of which the present application is the U.S. National Stage.
Don Ganem et al., "The Molecular Biology of the Hepatitis B Viruses", Annual Review Biochem., 56, pp. 651-693, 1987.

(Continued)

*Primary Examiner* — Phyllis G. Spivack
(74) *Attorney, Agent, or Firm* — Wenderoth, Lind & Ponack, L.L.P.

(57) ABSTRACT

A method for treating a liver disease such as hepatitis, comprising administering to a patient having the liver disease, an effective amount of a diarylsulfide or diarylether derivative having 2-amino-1,3-propanediol structure, and represented by the following formula (1):

(Chemical formula 1)

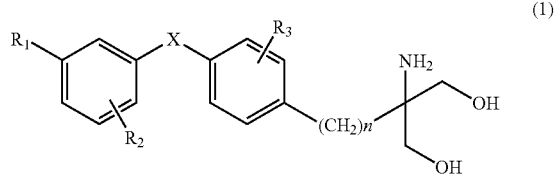

(1)

or a pharmaceutically acceptable salt thereof.

3 Claims, 2 Drawing Sheets

U.S. PATENT DOCUMENTS

| | | | |
|---|---|---|---|
| 2006/0161005 | A1 | 7/2006 | Doherty et al. |
| 2006/0166940 | A1 | 7/2006 | Buehlmayer et al. |
| 2006/0211656 | A1 | 9/2006 | Albert et al. |
| 2006/0211658 | A1 | 9/2006 | Hinterding et al. |
| 2006/0252741 | A1 | 11/2006 | Colandrea et al. |
| 2006/0264403 | A1 | 11/2006 | Albert |
| 2007/0010494 | A1 | 1/2007 | Ehrhardt et al. |
| 2007/0043014 | A1 | 2/2007 | Doherty et al. |
| 2007/0088002 | A1 | 4/2007 | Lynch et al. |
| 2007/0135501 | A1 | 6/2007 | Hinterding et al. |
| 2007/0149597 | A1 | 6/2007 | Nishi et al. |
| 2007/0167410 | A1 | 7/2007 | Pan et al. |
| 2007/0167425 | A1 | 7/2007 | Nakade et al. |
| 2007/0191468 | A1 | 8/2007 | Nishi et al. |
| 2007/0203100 | A1 | 8/2007 | Pan et al. |
| 2007/0225260 | A1 | 9/2007 | Hinterding et al. |
| 2008/0025973 | A1 | 1/2008 | Fleenor et al. |
| 2008/0027508 | A1 | 1/2008 | Chu |
| 2008/0032923 | A1 | 2/2008 | Kudou et al. |
| 2008/0153882 | A1 | 6/2008 | Nishi et al. |
| 2008/0161410 | A1 | 7/2008 | Kusters et al. |
| 2008/0200438 | A1 | 8/2008 | Albert et al. |
| 2008/0207584 | A1 | 8/2008 | Habashita et al. |
| 2008/0207941 | A1 | 8/2008 | Tsubuki et al. |
| 2008/0249093 | A1 | 10/2008 | Colandrea et al. |
| 2009/0023797 | A1 | 1/2009 | Azzaoui et al. |

FOREIGN PATENT DOCUMENTS

| | | |
|---|---|---|
| JP | 2002-53575 | 2/2002 |
| JP | 2002-316985 | 10/2002 |
| JP | 2003-137894 | 5/2003 |
| JP | 2003-267936 | 9/2003 |
| JP | 2004-137208 | 5/2004 |
| JP | 2004-307439 | 11/2004 |
| JP | 2004-307440 | 11/2004 |
| JP | 2004-307441 | 11/2004 |
| JP | 2004-307442 | 11/2004 |
| JP | 2005-47899 | 2/2005 |
| JP | 2005-247691 | 9/2005 |
| WO | 01/98301 | 12/2001 |
| WO | 03/029184 | 4/2003 |
| WO | 03/029205 | 4/2003 |
| WO | 2005/014525 | 2/2005 |
| WO | 2005/014603 | 2/2005 |
| WO | 2005/063671 | 7/2005 |
| WO | 2006/041015 | 4/2006 |
| WO | 2006/063033 | 6/2006 |
| WO | 2006/129688 | 12/2006 |
| WO | 2007/043433 | 4/2007 |
| WO | 2007/043568 | 4/2007 |
| WO | 2007/091501 | 8/2007 |

OTHER PUBLICATIONS

I Saito et al., "Hepatitis C virus infection is associated with the development of hepatocellular carcinoma", Proc. Natl. Acad. Sci., USA, vol. 87, pp. 6547-6549, Sep. 1990.

Mark E. Mailliard et al., "Suppressing Hepatitis B without Resistance—So Far, So Good", The New England Journal of Medicine, pp. 848-850, Feb. 27, 2003.

Michael W. Fried et al., "Peginterferon Alfa-2a Plus Ribavirin for Chronic Hepatitis C Virus infection", New England Journal of Medicine, vol. 347, No. 13, pp. 975-982, Sep. 26, 2002.

Francis V. Chisari, "Perspectives Series: Host/Pathogen Interactions", J. Clin. Invest., vol. 99, No. 7, pp. 1472-1477, Apr. 1997.

Takashi Kaneko et al., "Sphingosine-1-phosphate receptor agonists suppress concanavalin A-induced hepatic injury in mice", Biochemical and Biophysical Research Communications, vol. 345, pp. 85-92, 2006.

Rei Tsunematsu et al., "ConA Kan Shogai ni Okeru Men'eki Yokuseizai FTY720 no Koka ni Kansuru Kento", Acta Hepatologica Japonica, vol. 46, No. Supplement 2, p. A445, 'Kan P-207', Sep. 2005.

Michael A. Heneghan et al., "Current and Novel Immunosuppresive Therapy for Autoimmune Hepatitis", Hepatology, vol. 35, pp. 7-13, 2002.

Blam et al., Integrating Anti-Tumor Necrosis Factor Therapy in Inflammatory Bowel Disease: Current and Future Perspectives, Am. J. Gastroenterology, 2001, vol. 96, No. 7, pp. 1977-1997.

Keller et al., Immunomodulator FTY720 Induces Myofibroblast Differentiation via the Lysophospholipid Receptor S1P3 and Smad3 Signaling, Am. J. Pathology, Jan. 2007, vol. 170, No. 1, pp. 281-292.

Yasuyuki Igarashi, Sphingosine-1-Phosphate as an Intercellular Signaling Molecule, Ann. NY Acad. Sci., 1998, vol. 845, pp. 19-31.

Jacobs et al., Intramuscular Interferon Beta-1a for Disease Progression in Relapsing Multiple Sclerosis, Ann. Neurol., 1996, vol. 39, No. 3, pp. 285-294.

Weinshenker et al., A Randomized Trial of Plasma Exchange in Acute Central Nervous System Inflammatory Demyelinating Disease, Ann. Neurol., 1999, vol. 46, No. 6, pp. 878-886.

Okazaki et al., Molecular Cloning of a Novel Putative G Protein-Coupled Receptor Expressed in the Cardiovascular System, Biochem. and Biophys. Res. Commun., 1993, vol. 190, No. 3, pp. 1104-1106.

Klein et al., Total Synthesis and Antifungal Evaluation of Cyclic Aminohexapeptides, Bioorg. Med. Chem., 2000, vol. 8, pp. 167-1696.

Hashimoto et al., β-Phenylselenoalanine as a dehydroalanine precursor-efficient synthesis of alternariolide (AM-toxin I), Chem. Commun., 1996, pp. 1139-1140.

Levkau et al., High-Density Lipoprotein Stimulates Myocardial Perfusion in Vivo, Circulation, 2004, vol. 110, pp. 3355-3359.

Salomone et al., S1P$_3$ receptors mediate the potent constriction of cerebral arteries by sphingosine-1-phosphate, Eur. J. Pharmacol., 2003, vol. 469, pp. 125-134.

Kiuchi et al., Synthesis and Immunosuppressive Activity of 2-Substituted 2-Aminopropane-1,3-diols and 2-Aminoethanols, J. Med. Chem., 2000, vol. 43, pp. 2946-2961.

Brinkmann et al., The Immune Modulator FTY720 Targets Sphingosine 1-Phosphate Receptors, J. Biol. Chem., 2002, vol. 277, No. 24, pp. 21453-21457.

Sanna et al., Sphingosine 1-Phosphate (S1P) Receptor Subtypes S1P$_1$ and S1P$_3$, Respectively, Regulate Lymphocyte Recirculation and Heart Rate, J. Biol. Chem., Apr. 2, 2004, vol. 279, No. 14, pp. 13839-13848.

Forrest et al., Immune Cell Regulation and Cardiovascular Effects of Sphingosine 1-Phosphate Receptor Agonists in Rodents are Mediated via Distinct Receptor Subtypes, J. Pharm. Exp. Ther., 2004, vol. 309, No. 2, pp. 758-768.

George C. Ebers, Randomised double-blind placebo-controlled study of interferon β-1a in relapsing/remitting multiple sclerosis, Lancet, Nov. 7, 1998, vol. 352, pp. 1498-1501.

Takuwa et al., Subtype-specific, differential activities of the EDG family receptors for sphingosine-1-phosphate, a novel lysophospholipid mediator, Mol. Cell. Endocrinol., 2001, vol. 177, pp. 3-11.

Niessen et al., Dentritic cell PAR1-S1P3 signalling couples coagulation and inflammation, Nature, Apr. 3, 2008, vol. 452, No. 3, pp. 654-658.

IFNB Multiple Sclerosis Study Group, Interferon beta-1b is effective in relapsing-remitting multiple sclerosis. I. Clinical results of a multicenter, randomized, double-blind, placebo-controlled trial, Neurology, Apr. 1993, vol. 43, pp. 655-661.

Paty et al., Interferon beta-1b is effective in relapsing-remitting multiple sclerosis. II. MRI analysis results of a multicenter, randomized, double-blind, placebo-controlled trial, Neurology, Apr. 1993, vol. 43, pp. 662-667.

Johnson et al., Copolymer 1 reduces relapse rate and improves disability in relapsing-remitting multiple sclerosis: Results of a phase III multicenter, double-blind, placebo-controlled trial, Neurology, Jul. 1995, vol. 45, pp. 1268-1276.

Zivadinov et al., Effects of IV methylprednisolone on brain atrophy in relapsing-remitting MS, Neurology, 2001, vol. 57, pp. 1239-1247.

Goodin et al., Disease modifying therapies in multiple sclerosis; Report of the Therapeutics and Technology Assessment Subcommittee of the American Academy of Neurology and the MS Council for Clinical Practice Guidelines, Neurology, 2002, vol. 58, pp. 169-178.

Rudick et al., Management of Multiple Cclerosis, N. Engl. J. Med., Nov. 27, 1997, vol. 337, No. 22, pp. 1604-1611.

Daniel K. Podolsky, Inflammatory Bowel Disease, N. Engl. J. Med., Aug. 8, 2002, vol. 347, No. 6, pp. 417-429.

Kappos et al., Oral Fingolimod (FTY720) for Relapsing Multiple Sclerosis, N. Engl. J. Med., Sep. 14, 2006, vol. 355, No. 11, pp. 1124-1140.

Viscido et al., Inflammatory bowel diseases: clinical update of practical guidelines, Nucl. Med. Commun., 2005, vol. 26, No. 7, pp. 649-655.

Gon et al., $S1P_3$ receptor-induced reorganization of epithelial tight junctions comprises lung barrier integrity and is potentiated by TNF, PNAS, Jun. 28, 2005, vol. 102, No. 26, pp. 9270-9275.

Mandala et al., Alteration of Lymphocyte Trafficking by Sphingosine-1-Phosphate Receptor Agonists, Science, Apr. 2, 2002, vol. 296, pp. 346-349.

Hinterding et al., Synthesis of Chiral Analogues of FTY720 and its Phosphate, Synthesis, 2003, No. 11, pp. 1667-1670.

Campbell et al., The Synthesis of Novel Amino Acids via Hydroboration-Suzuki Cross Coupling, Tetrohedron Letters, 1999, vol. 40, pp. 5263-5266.

Collier et al., The direct synthesis of novel enantiomerically pure α-amino acids in protected form via suzuki cross-coupling, Tetrahedron Letters, 2000, vol. 41, pp. 7115-7119.

Long et al., Enantioselective syntheses of homophenylalanine derivatives via nitron 1,3-dipolar cycloaddition reactions with styrenes, Tetrahedron Letters, 2001, vol. 42, pp. 5343-5345.

Shimizu et al., KRP-203, a Novel Synthetic Immunosuppressant, Prolongs Graft Survival and Attenuates Chronic Rejection in Rat Skin and Heart Allografts, Circulation, 2005, vol. 111, pp. 222-229.

Takahashi et al., A Novel Immunomodulator KRP-203 Combined with Cyclosporine Prolonged Graft Survival and Abrogated Transplant Vasculopathy in Rat Heart Allografts, Transplant. Proc., 2005, vol. 37, pp. 143-145.

International Preliminary Report on Patentability dated Apr. 17, 2008 together with English translation of PCT Written Opinion in the PCT application corresponding to the present U.S. application.

Julien Davaille et al., "Sphingosine 1-Phosphate Triggers Both Apoptotic and Survival Signals for Human Hepatic Myofibroblasts" J. Biol. Chem., vol. 277, No. 40, pp. 37323-37330 (2002.).

Rudick et al., Management of Multiple Sclerosis N. Engl. J. Med., Nov. 27 1997, vol. 337, No. 22, pp. 1604-1611.

Collier et al., the direct synthesis of novel enantiomerically pure α-amino acids in protected form via suzuki cross-coupling, Tetrahedron Letters, 2000, vol. 41, pp. 7115-7119.

Tsunematsu, Satoshi, et al., "ConA Kan shogai ni Okeru Men'eki Yokuseizai FTY720 no Koka ni Kansuru Kento", Acta Heptatologica Japonica, Sep. 2005, vol. 46, No. Supplement 2, pp. A445 (English translation).

* cited by examiner

THERAPEUTIC AGENT FOR TREATING LIVER DISEASE CONTAINING 2-AMINO-1,3-PROPANEDIOL DERIVATIVE AS ACTIVE INGREDIENT, AND METHOD FOR TREATING LIVER DISEASE

TECHNICAL FIELD

The present invention relates to a novel therapeutic agent for treating liver diseases that contains as an active ingredient a diarylsulfide or diarylether derivative having 2-amino-1,3-propanediol structure, the compound that act as a sphingosine-1-phosphate receptor agonist, or a pharmaceutically acceptable salt and hydrate thereof.

BACKGROUND ART

A liver disorder, hepatitis can be caused by viruses, alcohol and drugs. Of hepatitis of different etiology, viral hepatitis is most common. Viral hepatitis is caused by hepatitis viruses that infect the liver. In particular, hepatitis B and hepatitis C are known to lead not only to acute hepatic failure, but also to hepatic cirrhosis and liver cancer at a significantly high rate (Non-Patent Documents 1 and 2). Of the more than 40,000 deaths each year resulting from liver cancer and hepatic cirrhosis in Japan, approximately 70% are infected with hepatitis C virus and approximately 20% with hepatitis B virus (Non-Patent Document 3).

The therapeutic agents for hepatitis B and C have been intensively developed in recent years. However, even lamivudine, one of the most promising therapeutic agents for hepatitis B, is not effective to an extent that eliminates hepatitis B virus (HVB) from all of the patients (Non-Patent Document 4). Although the introduction of interferons (IFN) has brought about the recent advances in the treatment of hepatitis C, the combination therapy of IFN preparations and ribavirin is not effective enough (Non-Patent Document 5). Despite the progress of conventional therapeutic agents, many people persistently infected with the viruses are still in need of treatments since persistent hepatitis can lead to hepatic cirrhosis and, ultimately, to hepatic cell carcinoma.

Recently, viral hepatitis has been realized as a incomplete immunological interaction between the host and the viruses without viral elimination (Non-Patent Document 6). It is now believed that the viruses harm the liver cells not by directly damaging the liver cells, but as a result of immune responses in which host's immune cells such as cytotoxic T cells eliminate and destroy the infected liver cells. The ideal treatment for the viral hepatitis is of course the elimination of virus. As in hepatitis C, the viral load is not necessarily a function of the severity of inflammation in hepatitis B.

Asymptomatic HBV carriers do not have liver inflammation despite a high viral load. When elimination of the virus is impossible, another option is to keep patients in a state of asymptomatic HBV carrier in which the virus survives but does not cause inflammation. The present invention provides compounds that prevent the onset of liver inflammation by suppressing T-cell activation.

2-amino-1,3-propanediol derivatives described in the present application are already described compounds (Patent Documents 1 and 2) and are known to be useful as immunosuppressors. Nonetheless, there is no previous studies or reports that demonstrate their use against liver diseases or suggest their efficacy to suppress liver inflammation.

Non-Patent Document 1 Annu. Rev. Biochem. 56: 651 (1987)
Non-Patent Document 2 Proc. Natl. Acad. Sci. USA, 87: 6547 (1990)
Non-Patent Document 3 Sogo Rinsyo, 54: 449 (2005)
Non-Patent Document 4 N. Engl. J. Med., 348: 848 (2003)
Non-Patent Document 5 N. Engl. J. Med., 347: 975 (2002)
Non-Patent Document 6 J. Clin. Invest., 99: 1472 (1997)
Patent Document 1 WO 2003/029184 pamphlet
Patent Document 2 WO 2003/029205 pamphlet

DISCLOSURE OF THE INVENTION

Problems to be Solved by the Invention

It is an object of the present invention to provide a therapeutic agent for treating diseases in organs, especially liver diseases. The therapeutic agent contains as an active ingredient a sphingosine-1-phosphate receptor agonist, specifically, a diarylsulfide or a diarylether derivative having 2-amino-1,3-propanediol structure, and a pharmaceutically acceptable salt and hydrate thereof.

Means for Solving the Problem

The present inventors have devised the present invention based on our finding that diarylsulfide or diarylether derivatives having 2-amino-1,3-propanediol structure, the compounds that act as sphingosine-1-phosphate receptor agonists, as well as their pharmaceutically acceptable salts and hydrates, can be used as effective therapeutic agents for various diseases in organs, in particular liver diseases.

Accordingly, the present invention concerns the following:

1) A therapeutic agent for treatment of liver disease containing as an active ingredient a diarylsulfide or diarylether derivative having 2-amino-1,3-propanediol structure and represented by the following general formula (1):

(Chemical formula 1)

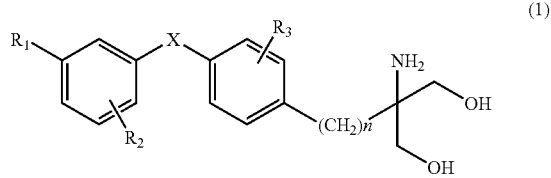

(wherein $R_1$ is a halogen atom, a trihalomethyl group, a hydroxyl group, a lower alkyl group having 1 to 7 carbon atoms, a substituted or unsubstituted phenyl group, an aralkyl group, a lower alkoxy group having 1 to 4 carbon atoms, a trifluoromethyloxy group, a phenoxy group, a cyclohexylmethyloxy group, a substituted or unsubstituted aralkyloxy group, a pyridylmethyloxy group, a cinnamyloxy group, a naphthylmethyloxy group, a phenoxymethyl group, a hydroxymethyl group, a hydroxyethyl group, a lower alkylthio group having 1 to 4 carbon atoms, a lower alkylsulfinyl group having 1 to 4 carbon atoms, a lower alkylsulfonyl group having 1 to 4 carbon atoms, a benzylthio group, an acetyl group, a nitro group, or a cyano group; $R_2$ is a hydrogen atom, a halogen atom, a trihalomethyl group, a lower alkoxy group having 1 to 4 carbon atoms, a lower alkyl group having 1 to 7 carbon atoms, a phenethyl group, or a benzyloxy group; $R_3$ is a hydrogen atom, a halogen atom, a trifluoromethyl group, a lower alkoxy group having 1 to 4 carbon atoms, a hydroxyl group, a benzyloxy group, a lower alkyl group having 1 to 7 carbon atoms, a phenyl group, a lower alkoxymethyl group having 1 to 4 carbon atoms, or a lower alkylthio group having 1 to 4 carbon atoms; X is O, S, SO or $SO_2$; and n is an integer of 1 to 4), and a pharmaceutically acceptable salt and hydrate thereof.

2) The therapeutic agent for treatment of liver disease according to 1), wherein the derivative represented by the general formula (1) comprises as an active ingredient 2-amino-2-[4-(3-benzyloxyphenylthio)-2-chlorophenyl]ethyl-1,3-propanediol, and a pharmaceutically acceptable salt and hydrate thereof.

3) The therapeutic agent for treatment of liver disease according to 1), wherein the compound represented by the general formula (1) comprises as an active ingredient 2-amino-2-[4-(3-benzyloxyphenylthio)-2-chlorophenyl]ethyl-1,3-propanediol hydrochloride and a hydrate thereof.

4) The therapeutic agent for treatment of liver disease according to 1) to 3) above, wherein the liver disease is hepatitis, fatty liver, toxic liver failure, hepatic cirrhosis, or a diabetes-associated liver disease.

5) A method for treating liver disease using as an active ingredient a diarylsulfide or diarylether derivative having 2-amino-1,3-propanediol structure and represented by the following general formula (1):

(Chemical formula 2)

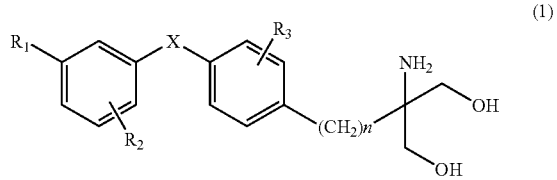

(1)

(wherein $R_1$ is a halogen atom, a trihalomethyl group, a hydroxyl group, a lower alkyl group having 1 to 7 carbon atoms, a substituted or unsubstituted phenyl group, an aralkyl group, a lower alkoxy group having 1 to 4 carbon atoms, a trifluoromethyloxy group, a phenoxy group, a cyclohexylmethyloxy group, a substituted or unsubstituted aralkyloxy group, a pyridylmethyloxy group, a cinnamyloxy group, anaphthylmethyloxy group, a phenoxymethyl group, a hydroxymethyl group, a hydroxyethyl group, a lower alkylthio group having 1 to 4 carbon atoms, a lower alkylsulfinyl group having 1 to 4 carbon atoms, a lower alkylsulfonyl group having 1 to 4 carbon atoms, a benzylthio group, an acetyl group, a nitro group, or a cyano group; $R_2$ is a hydrogen atom, a halogen atom, a trihalomethyl group, a lower alkoxy group having 1 to 4 carbon atoms, a lower alkyl group having 1 to 7 carbon atoms, a phenethyl group, or a benzyloxy group; $R_3$ is a hydrogen atom, a halogen atom, a trifluoromethyl group, a lower alkoxy group having 1 to 4 carbon atoms, a hydroxyl group, a benzyloxy group, a lower alkyl group having 1 to 7 carbon atoms, a phenyl group, a lower alkoxymethyl group having 1 to 4 carbon atoms, or a lower alkylthio group having 1 to 4 carbon atoms; X is O, S, SO or $SO_2$; and n is an integer of 1 to 4), and a pharmaceutically acceptable salt and hydrate thereof.

6) The method for treating liver disease according to 5) above, wherein the liver disease is hepatitis, fatty liver, toxic liver failure, hepatic cirrhosis, or a diabetes-associated liver disease.

Effect of the Invention

According to the present invention, there is provided a therapeutic agent for treating diseases in organs, especially liver diseases, that contains as an active ingredient a diarylsulfide or diarylether derivative having 2-amino-1,3-propanediol structure, the compound that act as a sphingosine-1-phosphate receptor agonist, and a pharmaceutically acceptable salt and hydrate thereof. According to the present invention, there is also provided an effective method for treating hepatitis, fatty liver, toxic liver failure, hepatic cirrhosis, diabetes-associated liver diseases and other liver diseases.

BEST MODE FOR CARRYING OUT THE INVENTION

Figure 1:
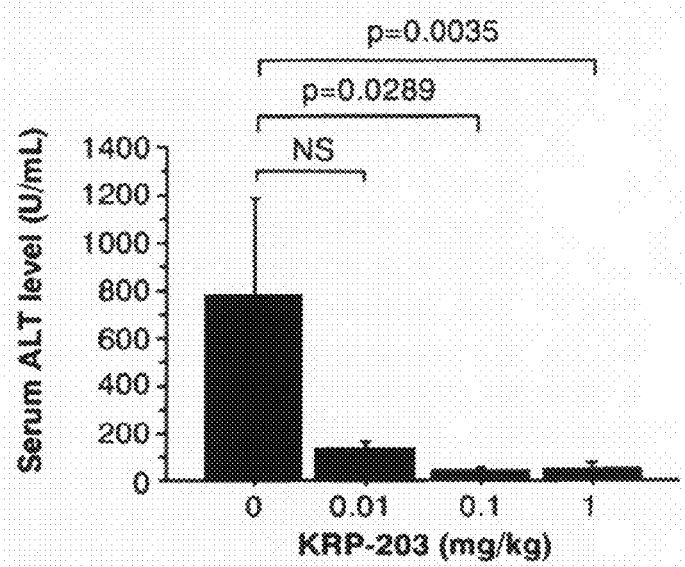
FIG. 1 is a graph showing the inhibitory effect of KRP-203 on the Con A-induced elevation of ALT level (p: Fisher's PLSD test).

The diarylsulfide or diarylether derivatives of the present invention have a 2-amino-1,3-propanediol structure and are novel sphingosine-1-phosphate receptor agonists. The compounds include those represented by the following general formula (1):

(Chemical formula 3)

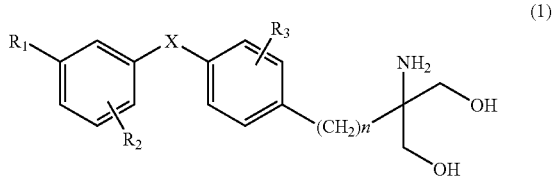

(1)

(wherein $R_1$ is a halogen atom, a trihalomethyl group, a hydroxyl group, a lower alkyl group having 1 to 7 carbon atoms, a substituted or unsubstituted phenyl group, an aralkyl group, a lower alkoxy group having 1 to 4 carbon atoms, a trifluoromethyloxy group, a phenoxy group, a cyclohexylmethyloxy group, a substituted or unsubstituted aralkyloxy group, a pyridylmethyloxy group, a cinnamyloxy group, a naphthylmethyloxy group, a phenoxymethyl group, a hydroxymethyl group, a hydroxyethyl group, a lower alkylthio group having 1 to 4 carbon atoms, a lower alkylsulfinyl group having 1 to 4 carbon atoms, a lower alkylsulfonyl group having 1 to 4 carbon atoms, a benzylthio group, an acetyl group, a nitro group, or a cyano group; $R_2$ is a hydrogen atom, a halogen atom, a trihalomethyl group, a lower alkoxy group having 1 to 4 carbon atoms, a lower alkyl group having 1 to 7 carbon atoms, a phenethyl group, or a benzyloxy group; $R_3$ is a hydrogen atom, a halogen atom, a trifluoromethyl group, a lower alkoxy group having 1 to 4 carbon atoms, a hydroxyl group, a benzyloxy group, a lower alkyl group having 1 to 7 carbon atoms, a phenyl group, a lower alkoxymethyl group having 1 to 4 carbon atoms, or a lower alkylthio group having 1 to 4 carbon atoms; X is O, S, SO or $SO_2$; and n is an integer of 1 to 4), or pharmaceutically acceptable salts and hydrates thereof.

In the general formula (1), the term "halogen atom" includes a fluorine atom, a chlorine atom, a bromine atom and an iodine atom. The term "trihalomethyl group" includes a trifluoromethyl group and a trichloromethyl group. The term "lower alkyl group having 1 to 7 carbon atoms" refers to a straight or branched hydrocarbon having 1 to 7 carbon atoms, such as methyl, ethyl, propyl, isopropyl, butyl, t-butyl, pentyl, hexyl and heptyl.

The term "substituted or unsubstituted phenoxy group" refers to a substituent consisting of a benzene ring that has at any of its ring positions a halogen atom (such as fluorine atom, chlorine atom, bromine atom and iodine atom), a trifluoromethyl group, a lower alkyl group having 1 to 4 carbon atoms or a lower alkoxy group having 1 to 4 carbon atoms. The term "aralkyl" as in "aralkyl group" and "aralkyloxy group" includes a benzyl group, a diphenylmethyl group, a phenethyl group and a phenylpropyl group. The term "lower alkyl" as in "lower alkoxy group having 1 to 4 carbon atoms," "lower alkylthio group having 1 to 4 carbon atoms," "lower alkylsulfinyl group having 1 to 4 carbon atoms" and "lower alkylsulfonyl group having 1 to 4 carbon atoms" refers to a straight or branched hydrocarbon having 1 to 4 carbon atoms, such as methyl, ethyl, propyl, isopropyl and butyl. The term "substituted or unsubstituted aralkyl group" refers to a substituent consisting of a benzene ring that has at any of its ring positions a halogen atom (such as fluorine atom, chlorine atom, bromine atom and iodine atom), a trifluoromethyl group, a lower alkyl group having 1 to 4 carbon atoms or a lower alkoxy group having 1 to 4 carbon atoms.

The pharmaceutically acceptable salts of the compounds of the present invention represented by the general formula (1) include acid addition salts, such as hydrochlorides, hydrobromides, acetates, trifluoroacetates, methanesulfonates, citrates and tartrates.

Specific examples of the compound of the general formula (1) include 2-amino-2-[4-(3-benzyloxyphenylthio)-2-chlorophenyl] ethyl-1,3-propanediol or hydrochlorides thereof.

The compounds of the present invention represented by the general formula (1) are disclosed, for example, in WO 03/029184 and WO03/029205 pamphlets and can be produced by the methods described in these publications.

The compounds of the present invention and their pharmaceutically acceptable salts and hydrates are effective in the treatment of various diseases in organs, in particular, liver diseases.

The therapeutic agents of the present invention may be administered either systemically or locally and either orally or parenterally. While the dosage form of the compounds may vary depending on the nature of the compounds, the compounds are typically formulated in oral or parenteral dosage forms. Specifically, the active ingredients may be mixed with pharmaceutically acceptable carriers, excipients, binders or diluents to prepare granules, powders, tablets, capsules, syrups, suppositories, suspensions or solutions.

While the clinical dose of the compounds of the present invention may vary depending on their applications, or the body weight, age and conditions of patients receiving the treatment, the compounds are typically administered at a single dose of 0.01 to 100 mg/patient and more preferably at a single dose of 0.1 to 5 mg/patient, once to three times daily.

EXAMPLES

The present invention will now be described in detail with reference to examples. Although the following examples will describe 2-amino-2-[4-(3-benzyloxyphenylthio)-2-chlorophenyl] ethyl-1,3-propanediol hydrochloride (which will be referred to as "KRP-203," hereinafter), one of the compounds represented by the general formula, these examples are not intended to limit the scope of the invention in any way.

Example 1

Inhibitory Effect on the Inflammation Induced by Concanavalin A

Male BALB/c mice, aged 8 to 12 weeks, were purchased from Charles River, Japan. Concanavalin A (referred to as "Con A," hereinafter) was dissolved in phosphate-buffered saline (PBS). 0.2 ml of this solution was intravenously administered to the animals to deliver 40 mg/kg of Con A. KRP-203 suspended in distilled water was orally administered at a dose of 0.1 mg/10 g body weight 24 hours before the administration of Con A. The animals were sacrificed 24 hours after the administration of Con A and the serum transaminase activity was measured. Also, the liver was perfused with 30 mL 0.1% EDTA-PBS to collect liver infiltrate (Eur. J. Immunol., 17: 37, 1987). To avoid contamination with lymphocytes in the periphery blood, the first 2.5 ml of the collected 0.1% EDTA-PBS was discarded. The collected cells were stained with anti-CD4 antibody, anti-CD8 antibody, anti-CD3 antibody, anti-CD45/B220 antibody, anti-CD11b antibody, anti-Ly-49C antibody and were counted with FACS Calibur.

Samples for histological analysis were prepared as follows: The liver was fixed in 10% formalin, embedded in paraffin, and sectioned. The resulting sections were stained with hematoxylin-eosin and observed for cell infiltration. The tissue was also frozen in liquid nitrogen in Tissue Tek, sectioned on Cryostat, and fixed in acetone. The resulting sections were immunostained with anti-mouse CD4 antibody, biotinylated anti-rat IgG antibody and streptavidin-alexa 488 and observed for infiltration of $CD4^+$ T cells.

(Results)

The ALT activity in the Con A-induced hepatitis model was measured and the results are shown in Table 1. FIG. 1 shows the serum ATL levels measured 24 hours after administration of Con A. The animals were orally administered KRP-203 24 hours before the administration of Con A. When liver inflammation is induced by Con A, ATL level is elevated, indicating liver damage.

Pre-administration of 0.1 mg/kg and 1 mg/kg KRP-203 significantly suppressed the elevation of ATL levels. A tendency of suppression was also observed in the group administered a low dose of 0.01 mg/kg.

The types and the numbers of cells that infiltrated the liver are shown in Table 1. The total number of infiltrated cells was decreased by about 50% in the group receiving KRP-203. Suppression of the infiltration of $CD3^+$ and $CD4^+$ T cells and $B220^+$ B cells was particularly significant in this group. Suppression of the infiltration of $CD8^+$ T cells and NK-T cells was minor. The infiltration of NK cells and monocytes was little affected.

TABLE 1

The types and numbers of the cells that infiltrated the liver

| Number of cells ($\times 10^5$) | Control | KRP-203 1 mg/kg |
|---|---|---|
| Total cells | 31.8 ± 8.4 | 16.3 ± 3.5‡ |
| $CD4^+$ | 2.97 ± 0.99 | 0.93 ± 0.33‡ |
| $CD8^+$ | 3.92 ± 0.96 | 2.53 ± 0.64 |
| $CD3^+ NK-$ | 8.24 ± 2.30 | 2.29 ± 0.53‡ |
| $NK^+ CD3-$ | 0.51 ± 0.24 | 0.40 ± 0.24 |
| $B220^+$ | 6.24 ± 2.06 | 2.06 ± 0.21‡ |
| $CD11b^+$ | 10.72 ± 4.36 | 8.47 ± 2.75 |

Figure 2:
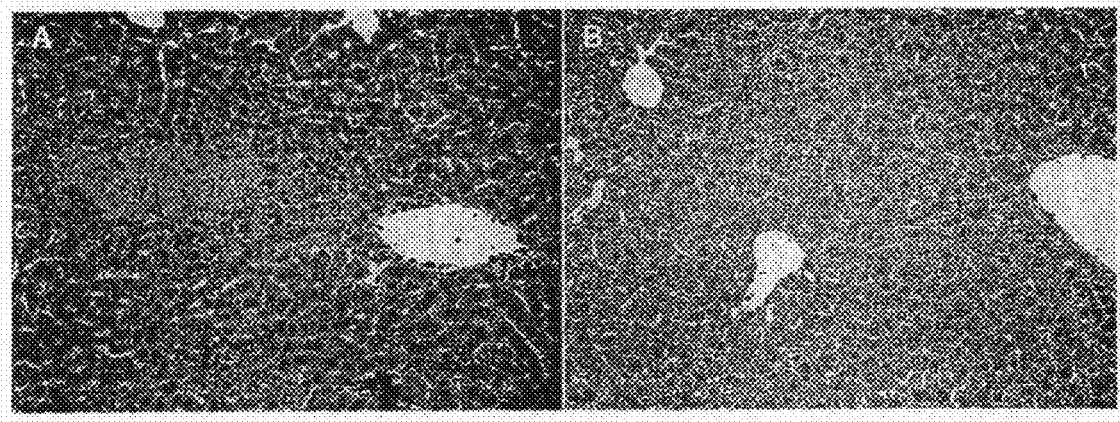
FIG. 2 shows micrographs showing the inhibitory effect of KRP-203 on the Con A-induced infiltration of inflammatory cells into the liver and the Con A-induced hepatocyte necrosis (hematoxylin-eosin staining, X100) (A: Control; B: KRP-203 administered at a dose of 1 mg/kg).
Figure 3:
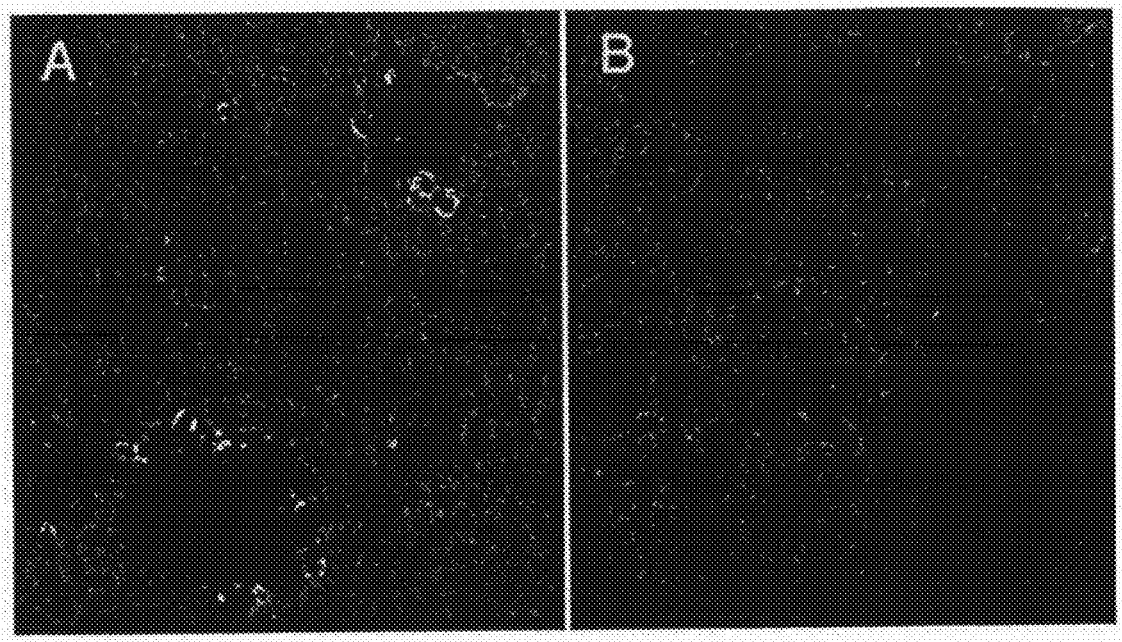
FIG. 3 shows micrographs showing the inhibitory effect of KRP-203 on the Con A-induced infiltration of $CD4^+$ T cells into the liver (immunostaining with anti-CD4 antibody, X200) (A: Control; B: KRP-203 administered at a dose of 1 mg/kg).

Histological appearances of the liver are shown in FIGS. 2 and 3. Con A-induced infiltration of monocytes and polymorphonuclear leukocytes as well as clusters of necrosis regions were observed in the liver of untreated group. Vacuolation of hepatocytes was also observed in this group (FIG. 2A). No significant infiltration of monocytes or necrotic changes was observed in the liver of KRP-203-treated mice (FIG. 2B). Immunostaining of $CD4^+$ T cells showed significant infiltration of $CD4^+$ T cells in the control group (FIG. 3A), but no infiltration in the KRP-203-treated group (FIG. 3B).

These observations indicate that KRP-203 prevents the onset and spreading of inflammation by suppressing infiltration of T cells into the liver and can thus be used in the prevention and treatment of hepatitis.

Example 2

Formulation Example

Capsule Formulation (Single Capsule)

Composition

| | |
|---|---|
| Compound (KRP-203) | 0.1 mg |
| D-mannitol | 247.5 mg |
| magnesium stearate | 2.5 mg |

Specifically, Compound was blended with D-mannitol. Magnesium stearate was then blended into this mixture to form a mixed powder. The resulting mixed powder was packaged in a capsule to make a capsule formulation.

INDUSTRIAL APPLICABILITY

As set forth, it has been demonstrated the compound of the present invention prevents the onset and spreading of liver inflammation in Con A-induced hepatitis model by suppressing infiltration and accumulation of T cells in the liver. Thus, the diarylsulfide or diarylether derivatives having 2-amino-1,3-propanediol structure, as well as pharmaceutically acceptable salts and hydrates thereof, are useful as a therapeutic agent for liver diseases.

Aside from liver diseases, the compounds of the present invention are effective against diseases in other organs whose pathology primarily involves activated lymphocytes. Among those diseases are renal diseases such as glomerular nephritis and tubulointerstitial disorders, vascular diseases such as arteriosclerosis, other autoimmune organ injuries (hepatitis such as autoimmune hepatitis and primary biliary cirrhosis, pancreatitis such as insulin-dependent diabetes, thyroiditis such as Basedow's disease and Hashimoto's disease, nephritis, multiple sclerosis and myasthenia gravis), and renal or cardiac organ injuries associated with ischemia reperfusion-injury. The compounds of the present invention are also effective against diseases caused by the activation of lymphocytes during infection. Examples of such diseases include viral myocarditis; nephritis and toxic shock syndrome associated with *staphylococcus* infection; nephritis, toxic shock syndrome and psoriasis associated with *streptococcus* infection; *Yersinia* infection and Kawasaki's disease.

Thus, the diarylsulfide or diarylether derivatives having 2-amino-1,3-propanediol structure, and pharmaceutically acceptable salts and hydrates thereof provided in accordance with the present invention are useful as the therapeutic agent for various diseases in organs, especially liver diseases.

The invention claimed is:

1. A method for treating hepatitis which comprises administering to a patient having hepatitis, as an active ingredient, an effective amount of a diarylsulfide or diarylether derivative having 2-amino-1,3-propanediol structure and represented by the following formula (I):

(Chemical formula 1)

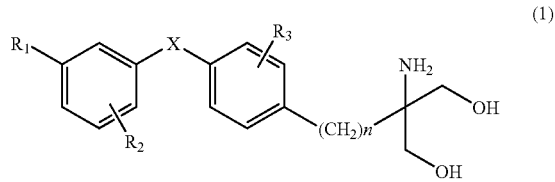

wherein $R_1$ is a halogen atom, a trihalomethyl group, a hydroxyl group, a lower alkyl group having 1 to 7 carbon atoms, a phenyl group, an aralkyl group, a lower alkoxy group having 1 to 4 carbon atoms, a trifluoromethyloxy group, a phenoxy group, a cyclohexylmethyloxy group, a aralkyloxy group, a pyridylmethyloxy group, a cinnamyloxy group, a naphthylmethyloxy group, a phenoxymethyl group, a hydroxymethyl group, a hydroxyethyl group, a lower alkylthio group having 1 to 4 carbon atoms, a lower alkylsulfinyl group having 1 to 4 carbon atoms, a lower alkylsulfonyl group having 1 to 4 carbon atoms, a benzylthio group, an acetyl group, a nitro group, or a cyano group; $R_2$ is a hydrogen atom, a halogen atom, a trihalomethyl group, a lower alkoxy group having 1 to 4 carbon atoms, a lower alkyl group having 1 to 7 carbon atoms, a phenethyl group, or a benzyloxy group; $R_3$ is a hydrogen atom, a halogen atom, a trifluoromethyl group, a lower alkoxy group having 1 to 4 carbon atoms, a hydroxyl group, a benzyloxy group, a lower alkyl group having 1 to 7 carbon atoms, a phenyl group, a lower alkoxymethyl group having 1 to 4 carbon atoms, or a lower alkylthio group having 1 to 4 carbon atoms; X is O, S, SO or $SO_2$; and n is an integer of 1 to 4, or a pharmaceutically acceptable salt thereof.

2. The method for treating liver disease hepatitis according to claim 1, wherein the active ingredient is 2-amino-2-[4-(3-benzyloxyphenylthio)-2-chlorophenyl]ethyl-1,3-propanediol, or pharmaceutically acceptable salt thereof.

3. The method for treating hepatitis according to claim 1, wherein the active ingredient is 2-amino-2-[4-(3-benzyloxyphenylthio)-2-chlorophenyl]ethyl-1,3-propanediol hydrochloride.

* * * * *